United States Patent
Morgan (10) Patent No.: US 8,025,686 B2
(45) Date of Patent: Sep. 27, 2011

(54) LIGHT CONDUCTOR AND TREATMENT FOR AILMENTS INVOLVING THE THROAT

(76) Inventor: Robert D. Morgan, Parma, ID (US)

(*) Notice: Subject to any disclaimer, the term of this patent is extended or adjusted under 35 U.S.C. 154(b) by 1057 days.

(21) Appl. No.: 11/849,592

(22) Filed: Sep. 4, 2007

(65) Prior Publication Data
US 2008/0058909 A1    Mar. 6, 2008

Related U.S. Application Data

(63) Continuation-in-part of application No. 11/516,178, filed on Sep. 5, 2006.

(51) Int. Cl.
*A61N 5/06* (2006.01)
(52) U.S. Cl. ............ 607/88; 607/92; 607/95; 128/898
(58) Field of Classification Search ............ 607/88–95; 606/15–18; 128/898; 385/100, 115, 123, 385/129, 900–902
See application file for complete search history.

(56) References Cited

U.S. PATENT DOCUMENTS

| | | | |
|---|---|---|---|
| 4,389,085 A * | 6/1983 | Mori | ............... 359/591 |
| 4,979,900 A | 12/1990 | Okamoto et al. | |
| 5,030,090 A | 7/1991 | Maeda et al. | |
| 5,445,608 A | 8/1995 | Chen et al. | |
| 6,129,721 A | 10/2000 | Katoaka et al. | |
| 6,572,609 B1 | 6/2003 | Farr et al. | |
| 6,942,657 B2 | 9/2005 | Sinofsky et al. | |
| 7,226,470 B2 * | 6/2007 | Kemeny et al. | .................. 607/94 |
| 2005/0177208 A1 * | 8/2005 | Irwin | .............. 607/94 |
| 2007/0255266 A1 * | 11/2007 | Cumbie et al. | .................. 606/9 |

OTHER PUBLICATIONS

International Search Report of PCT/US07/77565.

* cited by examiner

*Primary Examiner* — Ahmed Farah
(74) *Attorney, Agent, or Firm* — Mayback & Hoffman, P.A.; Gregoery L. Mayback; Katie M. Blakley

(57) ABSTRACT

A device and method for treating a throat includes inserting a device into the mouth and throat of a user where the device has a curved light-collecting face, a first side wall attached to the light-collecting face, a second side wall opposing the first side wall, attached to and extending away from the light-collecting face and converging toward the first side wall, an upper wall attached to the light-collecting face, a lower wall opposing the upper wall and attached to the light-collecting face, where the lower wall includes a first portion converging toward a first portion of the upper wall and a light emitter coupled to the first side wall, the second side wall, the upper wall, and the lower wall.

17 Claims, 7 Drawing Sheets

LIGHT CONDUCTOR AND TREATMENT FOR AILMENTS INVOLVING THE THROAT

CROSS-REFERENCE TO RELATED APPLICATIONS

This application is a continuation-in-part of application Ser. No. 11/516,178, filed Sep. 5, 2006, entitled "Light Conductor and Treatment for Ailments Involving the Throat", the complete disclosure of which is hereby incorporated by reference herein.

FIELD OF THE INVENTION

The present invention relates to a device used to irradiate and reduce or eliminate harmful bacteria and other "germs" that may reside in the rear mouth and throat area. More specifically, the invention relates to a self-contained device, capable of being used by one individual without assistance, wherein natural sunlight is transmitted to the throat area to accomplish the desired result. Upon viewing this disclosure, the invented device will be recognized as extremely useful by those persons wishing to accomplish self-healing methods for afflictions such as a sore throat without resorting to the typical drugs and antibiotics consumed for such purposes.

BACKGROUND OF THE INVENTION

U.S. Pat. No. 4,979,900, Okamoto, et al., addresses a root canal sterilization method, wherein a hand-held light guide attached to a counter-top UV generating means is used. This device is designed to be used by a dentist and does not permit use of natural sunlight.

U.S. Pat. No. 5,030,090, Maeda, et al., addresses a toothbrush connected to a power source by a power supply cord, which toothbrush uses optic fibers to admit irradiating light to the teeth. This device is designed to be used to cleanse the teeth and does not permit of use of natural sunlight.

U.S. Pat. No. 5,445,608, Chen, et al., addresses an implantable probe comprising LED's or LD's used to emit irradiating light to various tissues of the body for extended periods of time. This device is designed to be used on a long-term basis within the body and does not permit of use of natural sunlight.

SUMMARY OF THE INVENTION

The present invention relates generally to devices used to irradiate harmful bacteria and other "germs" within the human mouth and throat. The invented device, called a "light conductor" or "light conductor device" utilizes light to treat infections and eliminate harmful germs and bacteria within the human body, with natural sunlight being the especially-preferred light source and other sources of UV-spectrum light being alternative sources.

The invented device may be used safely by an individual, without assistance, to treat infections by reducing or eliminating bacteria or other microorganisms that are susceptible to sunlight, specifically within the rear mouth and upper throat areas. The invented device may be used as a supplement to, or instead of, conventional and/or homeopathic treatments and medicines. The inventor believes that treatment at home, using the invented device, may help prevent or at least postpone the need for doctor visits, emergency room visits, and antibiotics.

The invented device may help those who are traveling or are far away from medical care, for example, those who are hiking, sailing, or traveling or living in remote regions. Further, the inventor believes that some embodiments may be effective in treating, reducing or eliminating the bacteria in the mouth that cause many cases of "bad breath."

The invented device is held in the mouth so that an elongated portion of the device extends at least to the rear of the mouth and preferably into the upper region of the throat. The device is adapted to receive natural sunlight at its outer, distal end and to carry it to its proximal end inside the user's throat. The distal end extending outside the mouth is placed in the sunlight, and the sunlight travels through the device to the proximal end inside the rear of the mouth or throat, from which the sunlight radiates. The proximal end is preferably designed to radiate light in many directions at the same time, so that the natural sunlight reaches much of the surface of the rear mouth and upper throat. By virtue of sunlight's natural tendency to kill or otherwise inactivate micro-organisms, the sunlight reduces or eliminates the micro-organisms causing the sore throat and illness.

The preferred embodiments are larger at the distal, sunlight-collecting end, thence tapering along the length of the device to the proximal, sunlight-emitting end. The preferred embodiments are preferably constructed of optically clear plastic and are also preferably at least somewhat flexible, permitting comfortable insertion within the mouth and at least some conforming to the interior contours of same. The optically clear plastic may be in the form, for example, of a single piece that forms the entire or substantially the entire body of the light conductor, or a bundle or group of light fibers extending along the length of the body, as will be understood by one of skill in the fiber optics.

Preferably, the preferred light conductor has no power source except that it receives and transmits sunlight, for example, the preferred light conductor has no battery and no electrical connection. The preferred sunlight conductor has no light-bulbs, no light-emitting diodes, and no other devices that create or emit WV or other radiation except for structure and material from which sunlight may radiate.

The elongated light conductor structure is adapted to extend through the user's mouth and to the upper throat area, preferably with minimal, or at least comfortable, contact with the tongue and the throat, by means of the light conductor having a slightly curved shape and a size, shape, and thickness that fit well over the tongue and into the throat. Preferably, the light conductor is long enough to extend past all or a substantial portion of the tongue, and is of proportions, shape, and flexibility or texture preferably do not trigger a gag reflex in most people. The light conductor may be shorter than that shown in the drawings for users that may comfortably place a device in their mouth but feel they must keep it slightly forward of the throat. Also, the light conductor may optionally be rigid or substantially rigid, but this may tend to cause discomfort or gag reflex in more people.

The distal, light-collecting end need not be large or have a large surface area, as the preferred optically-clear plastic, once hit by sunlight, will carry the light to the proximal end. The distal end may be a small member, plate, or other protrusion that extends only 1-4 inches from the mouth, for example. The optically-clear plastic of the distal end is uncovered and unsheathed, so that all of it, or a substantial portion of it, is exposed to light when the user stands in the sunlight.

The middle portion of the tubular structure, between the distal and proximal ends, may be covered with a thin layer of opaque material, preventing sunlight captured at the distal end from exiting the device until said sunlight reaches and exits the proximal end of the tube.

The device may comprise some structure for helping the user position the light conductor in his/her mouth, for example, a positioner for placement at the outside of the lips and/or a positioner for being bitten or clenched between the teeth. In the embodiments shown, a ring is placed around and affixed to the light conductor, in close proximity to the distal end, wherein said structure is comprised of soft, pliable and flexible material upon which the teeth are closed or clenched to aid in keeping the light conductor at the proper attitude within the mouth and allowing hands-free use of the device. This positioner structure, and the other portions of the light conductor, should be waterproof, easily cleaned, and resistant to available cleaning aids such as soaps and detergents.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

DETAILED DESCRIPTION

While referring to the figures, there are shown several, but not the only, embodiments of the invented light conductor device used to kill, weaken, or otherwise reduce the effects of harmful bacteria or other germs in the throat. It is understood that the invented light conductor may also eliminate or reduce bacteria in the mouth or throat that are considered "good" bacteria or at least are considered not harmful. The preferred light conductor provides mild enough treatment that the "good" bacteria are not all destroyed as the harmful bacteria are reduced, and a more healthy balance of "good" bacteria and "bad" bacteria is reestablished.

Figure 1:
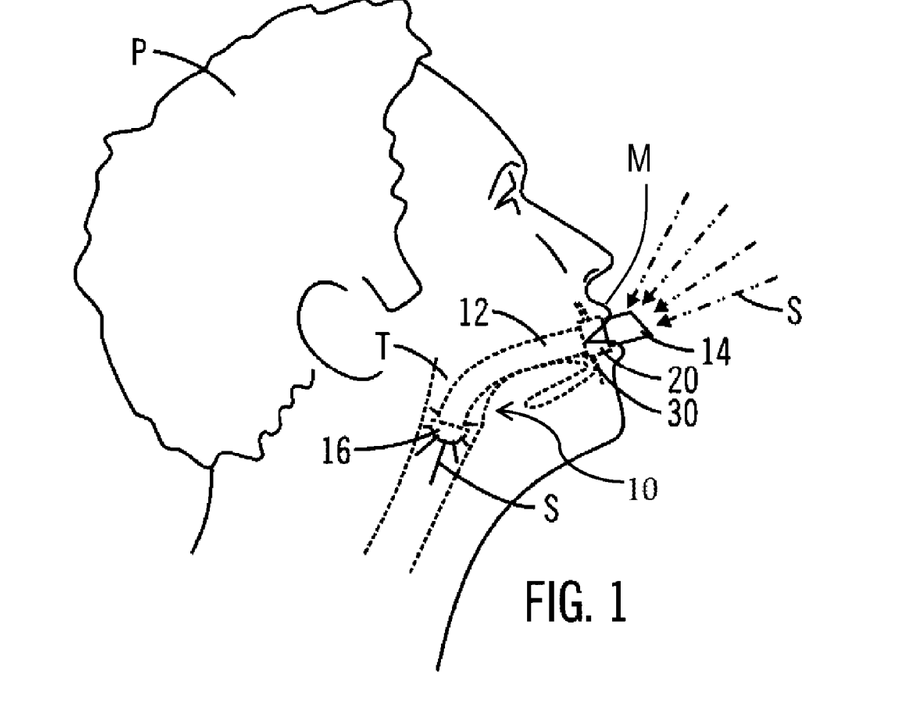
FIG. 1 is a side elevation view of a light conductor, according to one embodiment of the present invention, in use in a user's mouth and throat.

Referring now to FIG. 1, it may be observed that, in use, the light conductor assembly 10 is inserted into the mouth M such that the distal end 14 of light conductor body 12 remains outside the lips so that it may collect sunlight S. The proximal end 16 is located at the upper throat area T. Sunlight S travels the length of conductor body 12 and exits through proximal end 16 to irradiate the interior of the throat.

While the light conductor assembly 10 is portrayed in FIGS. 1-8 as a device that is fairly substantial in size relative to the mouth and throat, but many embodiments will be much smaller in diameter, for example, smaller in width and thickness all the way along the portion of the body adapted to be inside the mouth and throat. See, for example, FIGS. 15 and 16.

The teeth 30 of the person P are closed or clenched upon ring 20 to aid in keeping the light conductor 10 in the proper position within the mouth M, thereby permitting the user to have his or her hands free for other tasks.

Figure 2:
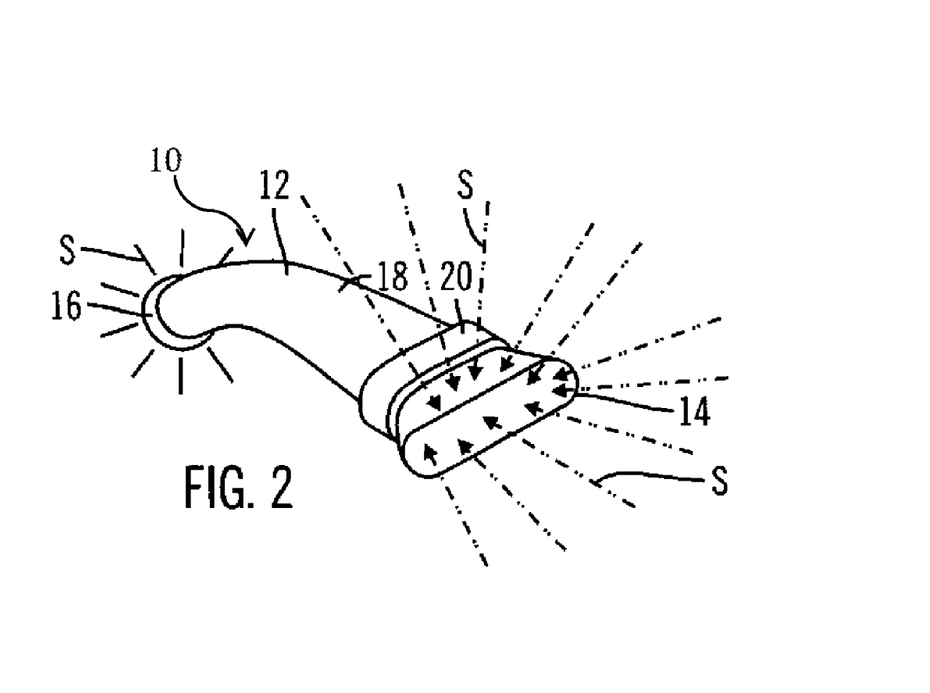
FIG. 2 is a perspective view of the light conductor of FIG. 1.

Referring now to FIG. 2, it will be seen that conductor body 12 is larger at the distal end 14 than at proximal end 16 and generally makes a more or less tapered transition in shape along its length from oval at the distal end 14 to round at the proximal end 16. This shape allows for a requisite amount of sunlight to be collected at distal end 14 and to be concentrated along the generally tapering length of light conductor body 12 to provide the necessary amount of sunlight exiting conductor body 12 at proximal end 16 to eliminate or reduce germs in the throat. FIG. 2 illustrates one, but not the only, shape with which light conductor 10 may be constructed, for example, the light conductor 10 may be generally square, triangular, round, or other shapes in cross-section. Further, for embodiments that are used to reduce or eliminate "bad breath," it may be beneficial to produce a light conductor that is slightly shorter in length, and has a proximal end that is flattened and relatively broad so that it emits light preferably all the way across the width of the tongue and preferably over the entire or substantially the entire surface of the tongue.

Figure 3:
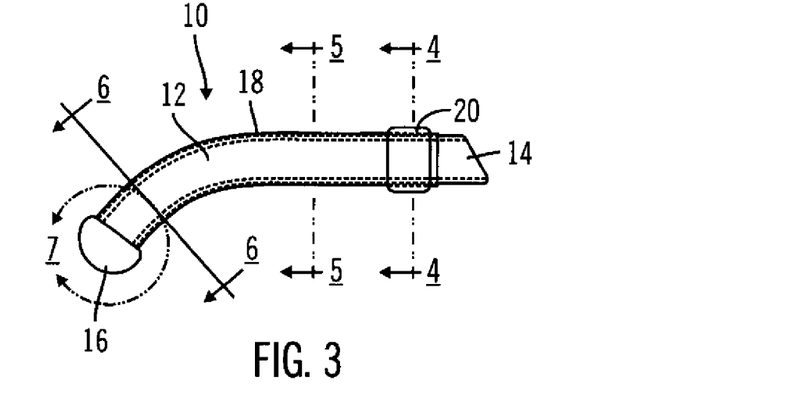
FIG. 3 is a side elevation view of the light conductor of FIGS. 1 and 2.
Figure 7:
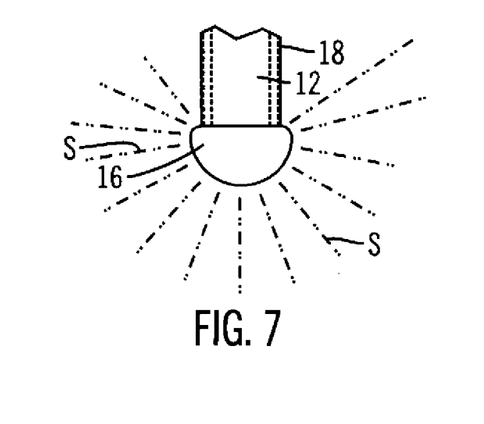
FIG. 7 is a partial side elevation view of the sunlight-emitting end of the embodiment of FIGS. 1-6.
Figure 8:
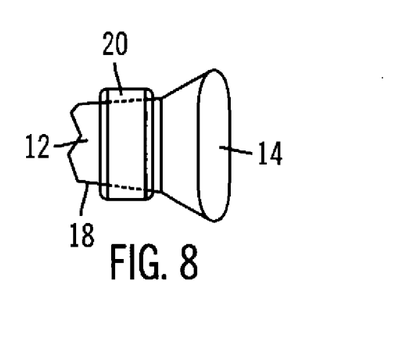
FIG. 8 is a partial plan view of the distal end of the embodiment of FIGS. 1-7.

Referring now to FIGS. 3, 7 and 8, it will be observed that conductor body 12 is designed, in a side profile, with a generally-curved shape to accommodate the curvature of the mouth and throat. Conductor body 12 is comprised of optically-clear plastic as will be understood by those in the fiber optics field after reading and viewing this application. The greater portion of conductor body 12, between distal end 14, at which sunlight is collected, and proximal end 16, at which sunlight is distributed into the throat, has disposed upon its outer surface cover 18, comprised of an opaque, preferably resilient and pliable material, through which sunlight cannot penetrate. Cover 18 prevents sunlight from radiating out of conductor body 12 until said light reaches proximal end 16.

Figure 4:
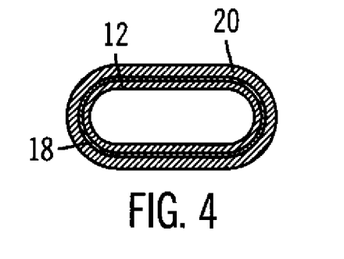
FIG. 4 is a cross-sectional elevation view of the light conductor of FIGS. 1-3, taken along the lines 4-4 in FIG. 3.
Figure 5A:
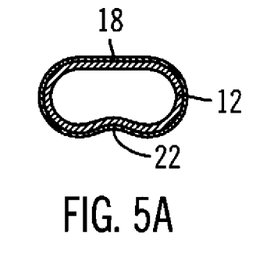
FIG. 5A is a cross-sectional elevation view of the light conductor of FIG. 1-3, taken along the lines 5-5 in FIG. 3, wherein the body of the light conductor is a solid piece of optically-clear plastic.

Referring now to FIGS. 3, 4 and 8, it may be seen that positioner ring 20, comprised of, but not limited to, a relatively soft pliable material such as rubber, is preferably adhesively attached to and surrounds body 12 and cover 18. A user may gently clench the upper and lower front teeth 30 upon positioner ring 20 (see FIG. 1), to aid in keeping the light conductor 10 at the proper attitude within the mouth, and, as aforementioned, allow hands-free use of the device. Referring now to FIG. 5, it will be observed that the cross-sectional shape of conductor body 12 may be constructed to permit easier insertion of the light tube 10 within the mouth. In this case, a depression 22 integrally molded within the lower portion of conductor body 12 may aid in the insertion, and/or comfortable resting, of the device over the top of the user's tongue. Other shapes and contours, including a thinner, smaller-diameter conductor, may be provided; many users may feel that a very thin conductor, such as less than ½ inch from top to bottom surface and/or less than ½ inch in diameter, is easier to tolerate in the mouth for the preferred several minutes of treatment time. See, for example, FIGS. 15 and 16. Also, the distal end and/or positioner for being gripped between the teeth, for example, may be smaller, thinner, and/or other shapes and sizes as desired and as effective for light conduction and/or comfortable use.

Figure 5B:
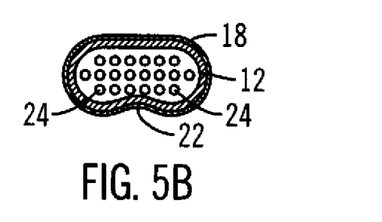
FIG. 5B is a cross-sectional elevation view according to a second embodiment of the present invention, wherein a cross-section as at line 5-5 in FIG. 3 would reveal a bundle of light fibers rather than a solid piece of optically-clear plastic.
Figure 6A:
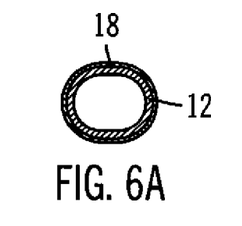
FIG. 6A is a cross-sectional elevation view of the light conductor in FIGS. 1-4, and 5A, viewed along the line 6-6 in FIG. 3.
Figure 6B:
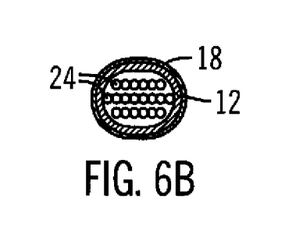
FIG. 6B is a cross-sectional elevation view according to the second embodiment, wherein a cross-section as at line 6-6 would reveal the light fibers (see also FIG. 5B).

Referring now to FIGS. 5B and 6B, an alternate embodiment of the invented device is shown wherein light transmitting light fibers 24, also constructed of optically clear plastic, are used to carry light from distal end 14 of body 12 to proximal end 16. The light fibers 24 may be received in a hollow casing that forms the conductor body, or otherwise contained inside the conductor body. The light transmitting tubes 24 fulfill all the functions of the solid or continuous optically-clear plastic body of the first embodiment described in the preceding narrative. Having a bundle of light fibers, which are themselves somewhat flexible, inside a generally flexible casing, may provide more comfort for many users.

Referring now to FIGS. 9 through 13, illustrated therein is a third embodiment of the present invention wherein a conductor 10' includes a storage battery power source 26 installed within body 12'. Electrical connections 28 are provided to connect said power source 26 with the light emitting diode or diodes 17 at the proximal end 16'. The diode(s) 17 may be UV-LED's or other diodes that emit light of a spectrum that damages or kills the bacteria and micro-organisms that are the target of the invention. Alternatively, other light sources may be used in embodiments of the invention, including various sources that emit light in a spectrum or part of a spectrum that are effective in damaging, reducing, and/or killing the bacteria or other micro-organisms that are the target of the invention. Also, as an alternative to the embodiments shown in the drawings, the invention may include embodiments using a "passive" light conductor such as that shown in FIGS. 1-8 (which typically relies on gathering of natural sunlight rather than light from a man-made source) combined with a separate but easily-attachable and easily-detachable "active" light source. Examples of such a light source might be a battery-powered or electrical-grid-powered light source that clips-on or is otherwise attachable to and removable from the passive light conductor, for example, attachable to the distal end so that it need not reach into the mouth of the user.

Alternatively, the battery and LED(s) may be combined together in a unit generally in the central portion of the body of the device, and fiber optic tubes or a larger member of optically-clear plastic may be interposed between the battery/LED unit and the light-emitting proximal end. Such light fibers, or other optically-clear member(s) would transmit light generated by the battery and LED unit to the proximal end, which end would preferably be an unsheathed, optically-clear plastic member adapted to radiate light out to the mouth and throat.

In these battery-powered embodiments, the general shape and principle of operation may remain the same as in the preferred embodiments, however, the light conductor body 12' may be comprised of an opaque material, with the exception of proximal end 16', as there is no sunlight being gathered at the distal end 14' for transmission through the body 12' of the conductor 10'. Light in these battery-powered embodiments is being transmitted from an LED in the proximal end 16' or inside the body 12', so light only needs to travel from the LED out of the proximal end 16' to the mouth and throat. If the LED is provided at the distal end 14', the light will only have to travel through the LED cover/casing 18'. If light travels from an LED(s) located away from the end of the conductor body 12', light fibers or a larger light-transmitting member may be provided to carry the light, and the body 12' itself will not necessarily need to be optically-clear.

Figure 9:
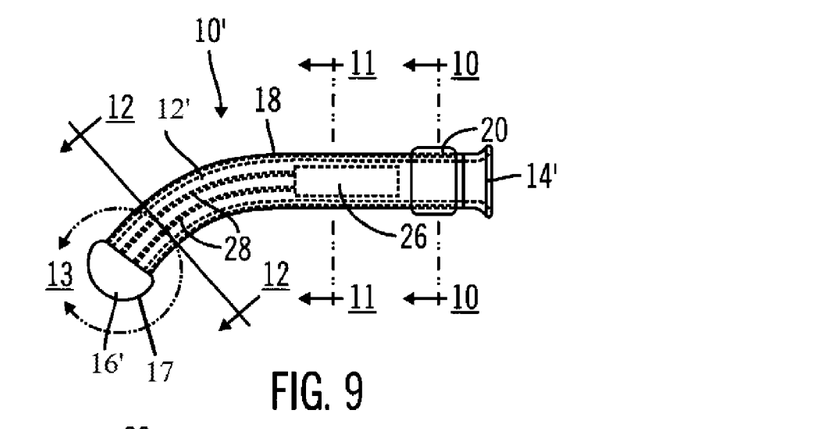
FIG. 9 is a side elevation view according to a third embodiment of the present invention, which comprises a battery and an LED.
Figure 10:
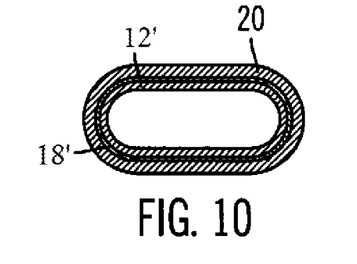
FIG. 10 is a cross-sectional view of the embodiment of FIG. 9, viewed along the line 10-10 in FIG. 9.
Figure 11:
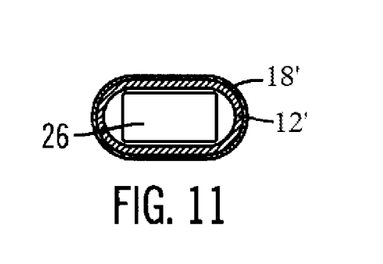
FIG. 11 is a cross-sectional view of the embodiment of FIGS. 9 and 10, viewed along the line 11-11 in FIG. 9.
Figure 12:
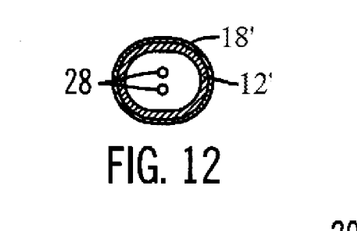
FIG. 12 is a cross-sectional elevation view of the embodiment of FIG. 9-11, viewed along the line 12-12 in FIG. 9.
Figure 13:
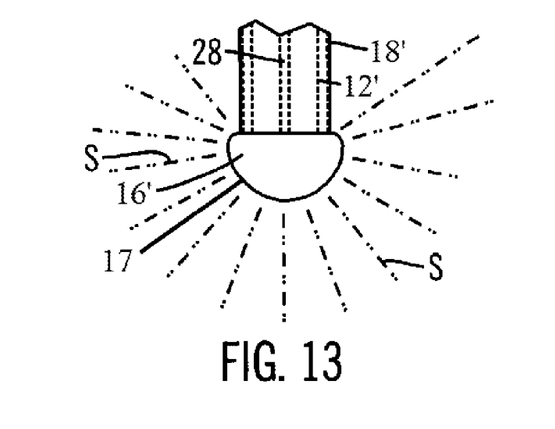
FIG. 13 is a partial side view of the proximal end of the embodiment of FIG. 9-12.
Figure 14:
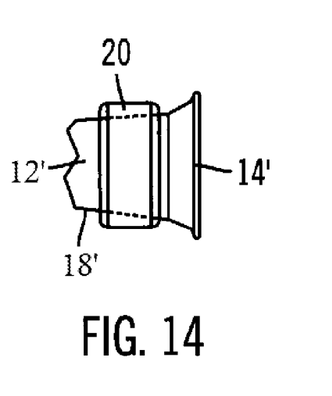
FIG. 14 is a partial plan view of the distal end of the embodiment of FIG. 9-13.

The distal end 14' of such embodiments, not being used to collect sunlight, may be of a different shape, for example, a flared or slightly enlarged end, preferably sufficient only to prevent swallowing or choking on the device by the user.

Figure 15:
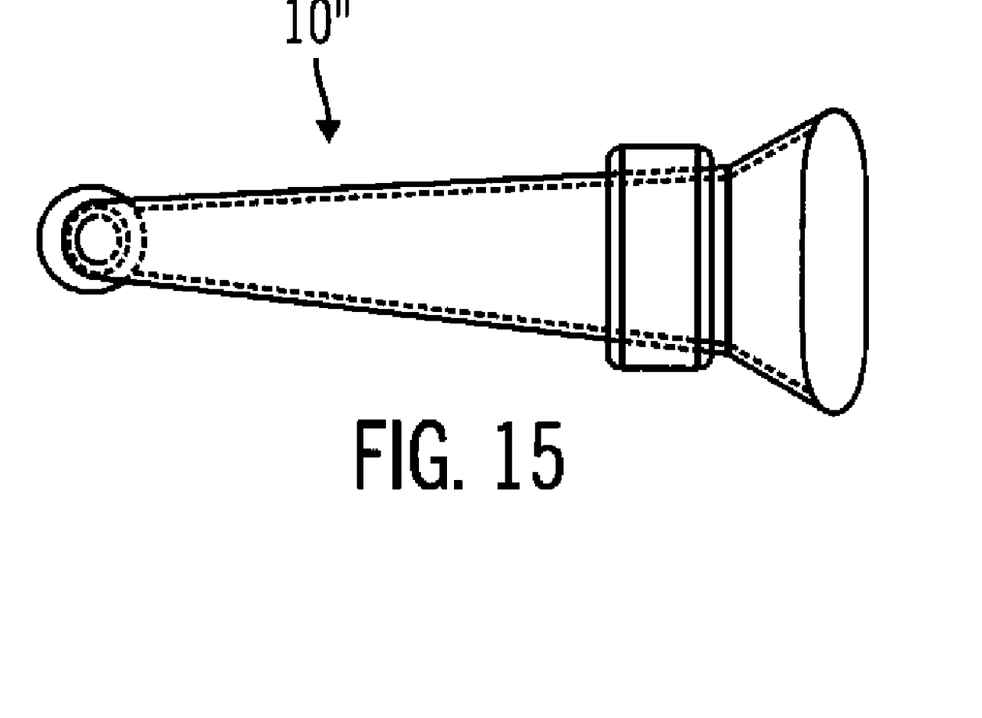
FIG. 15 is a top view of an alternative embodiment that tapers significantly in its side-to-side dimension and the top-to-bottom dimensions.
Figure 16:
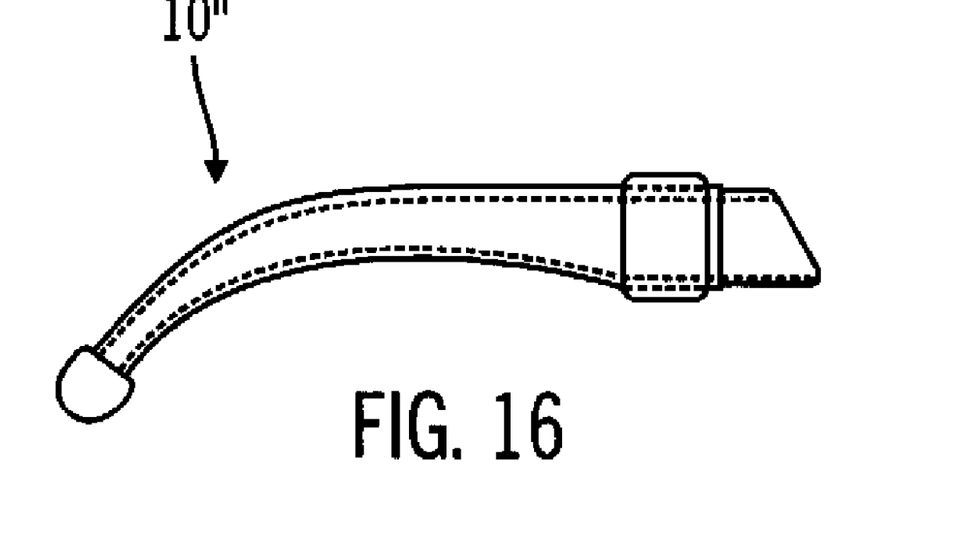
FIG. 16 is a side view of the embodiment of FIG. 15.

FIGS. 15 and 16 illustrate an especially-preferred substantially-tapered light conductor 10" according to another embodiment of the invention, which better illustrates how the dimensions may be reduced to be quite small, in order to be more comfortable and less intimidating to many users. The size of the preferred embodiments, especially the portion extending to the throat, may be reduced to be quite thin both in the side-to-side dimension and in the top-to-bottom dimension, as long as the light still travels efficiently from the distal end to the proximal end, as will be understood after viewing this disclosure by those in the field of fiber optics.

The main body of the light conductor may have alternative shapes and contours, and also the distal end and proximal end may have alternative shapes and contours. For example, while the proximal end shown in FIGS. 7 and 13 may be called generally semi-spherical or a portion of a sphere, other shapes may be used with a goal of emitting/radiating light in many directions from the proximal end. For example, emitting/radiating at least 180 degrees around the proximal end, and, more preferably, 180-340 degrees around the proximal end. An oval, elongated, cylindrical, or other proximal end shape may be used to provide surface area that does not focus the light in one direction but substantially all around the rear mouth and/or the upper throat.

In summary, many light conductors according to embodiments of the invention may be described as: a light conductor device for treating sore throat and other ailments caused by bacteria or other micro-organisms in the throat, the light conductor having an elongated body having a proximal end adapted for insertion into the human mouth and a distal end adapted for being outside the mouth and receiving natural sunlight, the elongated body comprising optically-clear plastic extending between the distal end and the proximal end so that said natural sunlight received by the distal end is transmitted to said proximal end from which it radiates out from the light conductor into the throat of the user to radiate said bacteria or other micro-organisms. The light conductor device may have no power source other than the sunlight being received on the distal end, and, preferably, the conductor device has no battery and no connection to any electrical power source.

The light conductor device may have an elongated body made substantially of optically-clear plastic, or an elongated body comprising light fibers which are the optically-clear plastic, both the plastic body or the body holding light fibers being adapted to carry the natural sunlight from the distal end to the proximal end. The proximal end preferably is adapted to radiate sunlight in greater than 180 degrees around the proximal end, for example, by means of being shaped generally as a part-spherical or semi-spherical surface, or a generally cylindrical surface, adapted to radiate sunlight to the throat. Most preferably, the proximal end is adapted to radiate sunlight almost 360 degrees (typically about 340 degrees, leaving room for the body of the device connecting to the proximal end) around the proximal end so that the sunlight reaches substantially the entire upper throat.

The device may be made in different sizes and lengths for children, teens, and adults, for example, ranging from about 4 to 12 inches long, and more typically, from about 5 to 8 inches long. The device may be curved on a radius between the proximal end and the distal end, so that the proximal end may curve down into the throat. Many of the embodiments will be curved on about a 4-6 inch radius.

The light conductor distal end typically only needs to protrude from the mouth (beyond the lips) about 1-4 inches, as sunlight will hit the distal end and, due to the natural properties of sunlight and the preferred materials of the device, will travel efficiently through the device to the proximal end. The user may want to tilt his/her head back slightly to allow the sun to hit a substantial portion of the distal end, as shown in FIG. 1. Alternatively, a larger plate or sun-collecting member may be integral with or attached to the distal end.

The user may find the invented device an easy-to-use self-treatment tool, and may find that even a few minutes of self-treatment will help. Use of the device does not require a doctor or nurse or other assistant, but users are encouraged to monitor their health and seek medical advice if the sore throat persists more than a few days. Typically, the inventor recommends 2-15 minutes of use per treatment, and more preferably, 3-5 minutes of use per treatment, with multiple treatments separated by ½-4 hours. The user should be careful not to overuse the device, due to possible concerns about overexposure to sunlight. The invented device is not intended for sterilization during root canals, or other dental work, and the invented device preferably does not include any tooth brushing member.

In the embodiments including a battery and one or more LED's, features similar to those of the sunlight-powered device may be included, for example, the part-spherical, semi-spherical, cylindrical, or semi-cylindrical proximal end, the curvature and/or contours and/or preferred (but not required) flexibility for making the device more comfortable in the mouth. One would expect that battery-powered embodiments would also be in the range of 4-12 (more preferably 5-8) inches long and curved on a 4-6 inch radius. The distal end of such embodiments could be smaller/shorter as it need not collect sunlight; for example, such distal ends may protrude about 0.5-2 (more preferably –0.5-1 inch) from the mouth.

Embodiments of the invention may include methods of using a light conductor to help cure sore throats or other illnesses. The methods may include not connecting the device to any external power source (except the sun). The preferred methods may include not treating the teeth, root canals, or sinuses, but, preferably, treating the throat.

Figure 17:
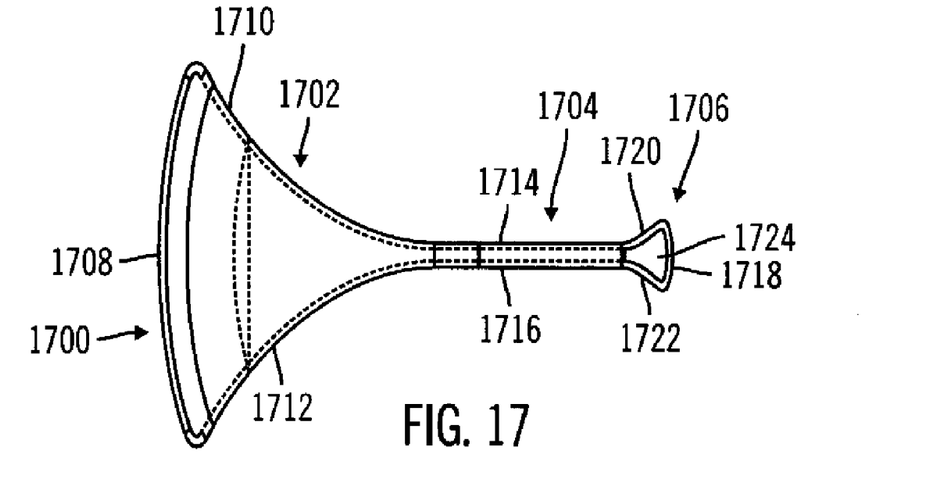
FIG. 17 is a top plan view of a light conductor, according to a fourth embodiment of the present invention.

FIG. 17 shows a top view of another embodiment of the present invention, which includes a light-collecting portion 1702, a light-conducting portion 1704, and a light-emitting portion 1706. The light-collecting portion 1702 includes a curved light-collecting face 1708. The curved light-collecting face 1708, in one embodiment, is a transparent material that allows light to pass through the face 1708 and into an interior (not shown in this view) of the inventive device 1700. The face 1708 is framed by a pair of side walls 1710 and 1712 that extend from the face 1708 and converge in an arcuate shape toward one another.

The side walls 1710 and 1712 flow into and are integral with a set of side walls 1714 and 1716 that frame the light-conducting portion 1704. The light-conducting portion 1704 provides a pathway for channeling light collected at the face 1708 to the light-emitting portion 1706, which will be described in the following paragraph. As can be seen by the top view of FIG. 17, the sidewalls of the light-conduction portion are substantially parallel to one another between the light-collecting portion 1702 and the light-emitting portion 1706, in other words, within the light-conducting portion 1704.

The light-emitting portion 1706 includes a curved transparent face 1718 that is framed by a pair of side walls 1720 and 1722 that diverge from one another along a path from the light-conducting portion 1704 to the face 1718. The diverging walls 1720 and 1722 allow light that is traveling along the light-conducting portion 1704 to disperse within the interior 1724 of the light-emitting portion 1706 and exit the curved face 1718 in an evenly distributed pattern.

Figure 18:
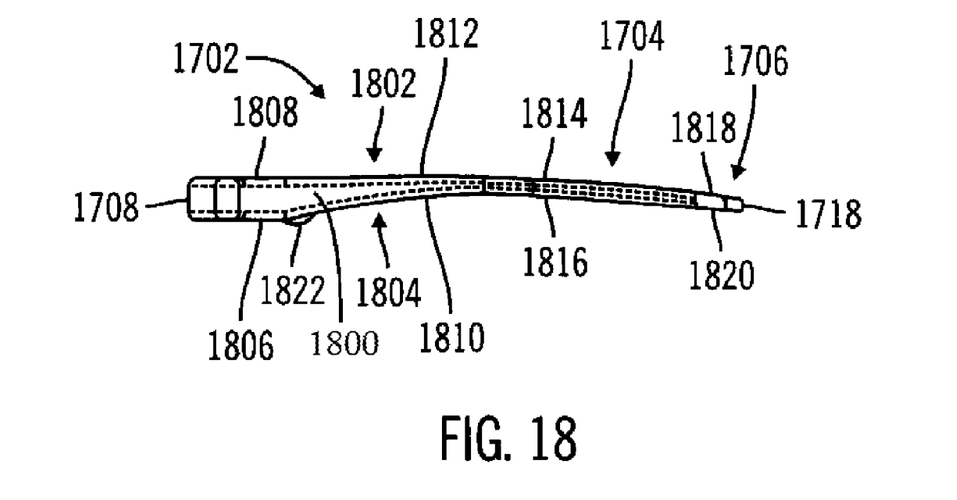
FIG. 18 is a side elevational view of the light conductor of FIG. 17.

FIG. 18 shows a side view of the embodiment of the inventive device shown in FIG. 17. As is shown in the side view, an upper wall 1802 and an opposing lower wall 1804 are attached to the light-collecting face 1708. The lower wall 1804 includes a first portion 1806 that is substantially parallel to a first portion 1808 of the upper wall 1802. The lower wall 1804 also includes a second portion 1810 that converges in a slightly arcuate shape toward a second portion 1812, also with a slightly arcuate shape, of the upper wall 1802. The upper 1802 and lower 1804 walls define an interior area 1800. The interior area 1800 is defined by a set of surfaces, which are the upper wall 1802, lower wall 1804, and side walls 1710 and 1712 (see FIG. 17). In one embodiment, these walls are polished so that light within the interior 1800 is refracted off of the surfaces thereof and is channeled to the light-emitting face 1718.

As is also shown in FIG. 18, the upper wall 1802 and opposing lower wall 1804 are seamlessly coupled to an upper wall 1814 and lower wall 1816 of the light-conducting portion 1704. The upper wall 1814 and lower wall 1816 of the light-conducting portion 1704 are substantially parallel to each other along the length of the light-conducting portion 1704.

In the embodiment shown in FIG. 18, the upper wall 1814 and lower wall 1816 of the light-conducting portion 1704 continue into the light-emitting portion 1706 and become upper wall 1818 and lower wall 1820 of the light-emitting portion 1706. Therefore, the light-emitting face 1718 is framed by side walls 1720 and 1722, upper wall 1818, and lower wall 1820.

Also shown in the side view of FIG. 18 is a protuberance 1822 extending from the lower wall 1804 of the light-collecting portion 1702 of the inventive device. The protuberance 1822 provides a tactile guide for a user to feel with his/her mouth and, therefore, know when the device is inserted a proper distance therein. The invention, however, is not so limited to the protuberance shown and can be any other raised area and shape or indented area or shape.

The embodiment of FIGS. 17 and 18 is particularly well suited for treating a throat. The light-emitting portion 1706 is small, in terms of both height and width, and can easily fit into the throat of a user without causing a gag reflex. The light-conduction portion 1704 is thin, flat, and long enough to extend into the throat and direct the light-emitting portion towards an area of the throat that requires treatment. In addition, the light-collecting portion 1702 is wide enough to not completely fit into a user's mouth and create a choking hazard. The width of the light-collecting portion 1702 also presents a large area for light collection. Furthermore, the protuberance 1822 provides a tactile indicator of when the device 1700 is inserted a sufficient distance into the user's throat.

In one embodiment, the device 1700 is made of a material that presents little impedance to the light rays entering the light-collecting face 1708 so that they are delivered with maximum intensity to and out of the light-emitting face 1718. One embodiment of the present invention also provides the upper wall 1808 in a transparent material that allows light to enter the device 1700 through the upper wall 1808 and from a direction above the device 1700. In this embodiment, the lower wall 1806 presents a reflective surface that will refract light that enters from the upper wall 1808 and cause it to be reflected back into the device 1700.

Figure 19:
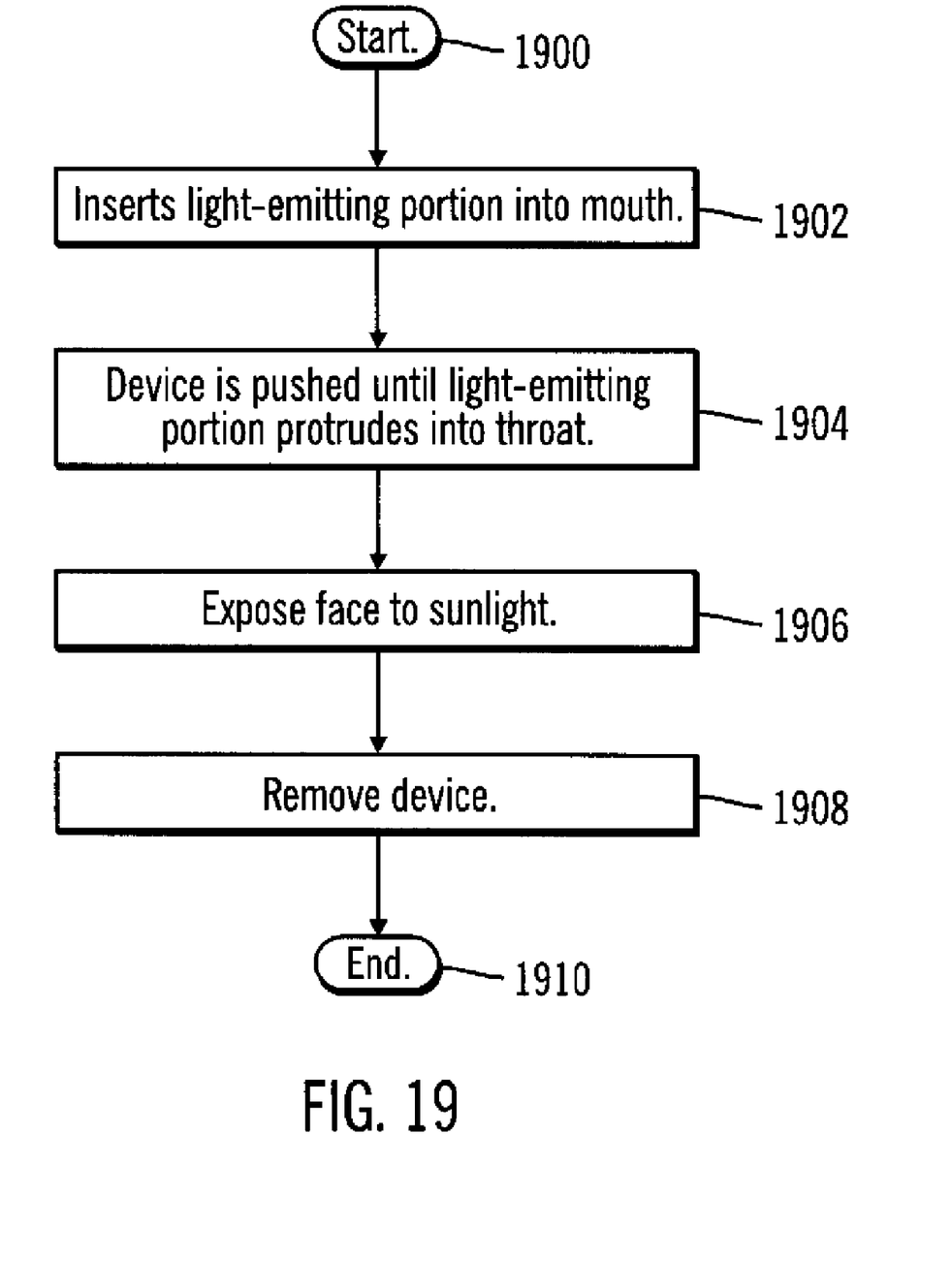
FIG. 19 is a process flow diagram illustrating one exemplary method for using the light conductor, according to an embodiment of the present invention.
Figure 20:
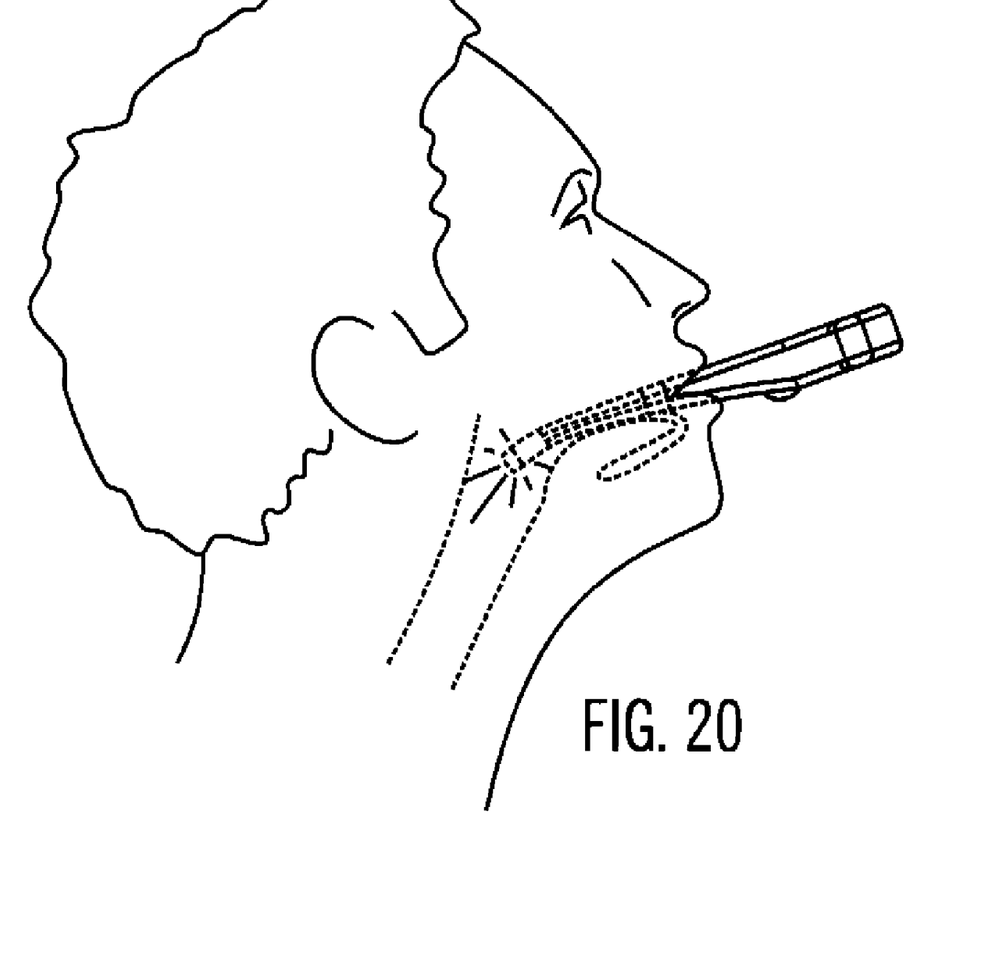
FIG. 20 is a side elevation view of the light conductor of FIGS. 17 and 18, according to one embodiment of the present invention, in use in a user's mouth and throat.

FIG. 19 is a process flow diagram describing a method for utilizing the inventive light-conducting device 1700 to treat a sore throat or other ailments caused by bacterial or other micro-organisms in the throat. The flow starts at step 1900 and moves directly to step 1902 where a user inserts the light-emitting portion of the device 1700 into their mouth. In step 1904, the device 1700 is pushed deeper into the mouth until the light-emitting portion protrudes into the throat. The user then, in step 1906, exposes the light-collecting face 1708 to natural or manufactured sunlight for a period of time selected for providing one dose of treatment to the back of the throat. In step 1908, the device is removed from the user's throat and mouth. The process ends at step 1910.

Although this invention has been described above with reference to particular means, materials and embodiments, it is to be understood that the invention is not limited to these disclosed particulars, but extends instead to all equivalents within the scope of the following claims.

What is claimed is:

1. A device for treating a throat, the device comprising:
   a curved light-collecting face;
   a first side wall adjacent the light-collecting face;
   a second side wall opposing the first side wall and adjacent the light-collecting face, both the first side wall and the second side wall extending away from the light-collecting face and converging toward one another;
   an upper wall adjacent the light-collecting face;
   a lower wall opposing the upper wall and adjacent the light-collecting face, the lower and upper walls each including a first portion converging toward one another; and
   a light emitter coupled to the first side and second side walls, the upper wall, and the lower wall, the light emitter including:
      a curved transparent light emitter face; and
      a light dispersing chamber having two opposing side walls diverging away from one another in a direction toward the light emitter face.

2. The device according to claim 1, wherein the lower wall further includes a second portion substantially parallel to a second portion of the upper wall.

3. The device according to claim 1, wherein the light-collecting face is framed by the first side wall, the second side wall, the upper wall and the lower wall.

4. The device according to claim 1, wherein:
   at least a portion of each of the first side wall, the second side wall, the upper wall, and the lower wall defines a light conduction portion.

5. The device according to claim 1, further comprising:
   a protuberance on the bottom surface.

6. The device according to claim 1, wherein at least a portion of the upper wall and at least a portion of the lower wall is arcuate shaped.

7. A device for treating a throat, the device comprising:
   a light-collecting portion including:
      a curved transparent face;
      a first side wall;
      a second side wall extending away from the face and converging toward the first side wall;
      an upper wall; and
      a lower wall substantially parallel to the upper wall;
   a light-emitting portion including:
      a curved transparent face;
      a pair of diverging side walls;
      an upper wall; and
      a lower wall substantially parallel to the upper wall; and
   a light-communication portion optically connecting the transparent face of the light-collecting portion and the transparent face of the light-emitting portion.

8. The device according to claim 7, wherein the light-communication portion further comprises:
   an upper wall coupling the upper wall of the light-collecting portion to the upper wall of the light-emitting portion;
   a lower wall coupling the lower wall of the light-collecting portion to the lower wall of the light-emitting portion;
   a first side wall coupling the first side wall of the light-collecting portion to the first side wall of the light-emitting portion; and
   a second side wall coupling the second side wall of the light-collecting portion to the second side wall of the light-emitting portion.

9. The device according to claim 8, wherein the upper wall of the light-communication portion and the lower wall of the light-communication portion are arcuate shaped.

10. The device according to claim 8, wherein the light-communication portion is made of optically-clear plastic adapted to carry light from the light-collecting portion to the light-emitting portion.

11. The device according to claim 8, further comprising:
   a protuberance on the lower wall of one of the light-collecting portion and the light-communicating portion.

12. The device according to claim 8, wherein the lower wall of the light-communicating portion and the upper wall of the light-communicating portion converge toward one another.

13. The device according to claim 12, wherein the continuous light-conducting pathway comprises a set of light-reflective interior surfaces.

14. The device according to claim 7, wherein the light-communication portion is a continuous light-conducting pathway between the light-collecting portion and the light-emitting portion.

15. The device according to claim 7, wherein the light-collecting portion is larger than a user's mouth.

16. A method for treating a throat, the method comprising:
   inserting a light-emitting portion of a throat-treating device into a throat area of a user, the device including:
      a curved light-collecting face;

a first side wall adjacent the light-collecting face;

a second side wall opposing the first side wall and adjacent the light-collecting face, both the first side wall and the second side wall extending away from the light-collecting face and converging toward one another;

an upper wall adjacent the light-collecting face; and a lower wall opposing the upper wall and adjacent the light-collecting face, the lower and upper walls each including a first portion converging toward one another; and the light-emitting portion including:

a curved transparent light emitter face;

a pair of opposing and diverging side walls;

an upper wall; and a lower wall substantially parallel to the upper wall; and exposing the light-collecting face of the device to sunlight.

17. The method according to claim 16, further comprising:

carrying out the exposing step in sunlight to transmit collected sunlight by the light-collecting face to the transparent light emitter face.

* * * * *